United States Patent
Harding (12)

(10) Patent No.: US 6,632,803 B1
(45) Date of Patent: Oct. 14, 2003

(54) PHARMACEUTICAL FORMULATIONS CONTAINING VORICONAZOLE

(75) Inventor: Valerie Denise Harding, Sandwich (GB)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 09/402,289

(22) PCT Filed: Jun. 2, 1998

(86) PCT No.: PCT/EP98/03477

§ 371 (c)(1),
(2), (4) Date: Sep. 29, 1999

(87) PCT Pub. No.: WO98/58677

PCT Pub. Date: Dec. 30, 1998

(30) Foreign Application Priority Data

Jun. 21, 1997 (GB) .............................................. 9713149

(51) Int. Cl.⁷ ..................... A61K 31/715; A61K 31/519
(52) U.S. Cl. ........................ 514/58; 514/256; 514/340
(58) Field of Search ........................... 514/58, 256, 340

(56) References Cited

U.S. PATENT DOCUMENTS

| 5,134,127 A | * | 7/1992 | Stella et al. | ................... | 514/58 |
| 5,278,175 A | * | 1/1994 | Ray et al. | ................... | 514/340 |
| 5,376,645 A | * | 12/1994 | Stella et al. | ................... | 514/58 |
| 5,567,817 A | * | 10/1996 | Ray et al. | ................... | 544/333 |
| 5,773,443 A | * | 6/1998 | Ray et al. | ................... | 514/256 |

FOREIGN PATENT DOCUMENTS

| EP | 0149147 | 3/1989 |
| EP | 0357241 | 3/1990 |
| EP | 0440372 | 8/1991 |
| EP | 0149197 | 1/1997 |
| WO | WO85/02767 | 7/1985 |
| WO | WO9111172 | 8/1991 |
| WO | WO9402518 | 2/1994 |
| WO | WO97/01552 | 1/1997 |
| WO | WO9701552 | 1/1997 |
| WO | WO97/28169 | 8/1997 |

OTHER PUBLICATIONS

Szejtli J. Pharm Tech, Aug. 1991, pp. 24–38.
Barry A.L. & Brown S.D., Antimicrobial Agents & Chemotherapy, Aug. 1996, vol. 40 (8), pp. 1948–1949.
George D., Minter P., & Andriole V.T., Antimicrobial Agents & Chemotherapy, Jan. 1996, vol. 40 (1), pp. 86–91.

* cited by examiner

Primary Examiner—Kathleen K. Fonda
Assistant Examiner—Leigh C. Maier
(74) Attorney, Agent, or Firm—Peter C Richardson; Gregg C Benson; James T Jones

(57) ABSTRACT

The invention provides pharmaceutical formulation comprising voriconazole, or a pharmaceutically acceptable derivative thereof, and a sulfobutylether β-cyclodextrin.

6 Claims, No Drawings

PHARMACEUTICAL FORMULATIONS CONTAINING VORICONAZOLE

CROSS REFERENCE TO RELATED APPLICATION

This application is the National Stage filing under 35 USC §371 based on PCT/EP98/03477, published as WO 98/58677, which was filed internationally on Jun. 2, 1998.

This invention relates to a new pharmaceutical formulation of voriconazole with a sulphobutylether β-cyclodextrin.

Voriconazole is disclosed in European Patent Application 0440372 (see Example 7). It has the following structure:

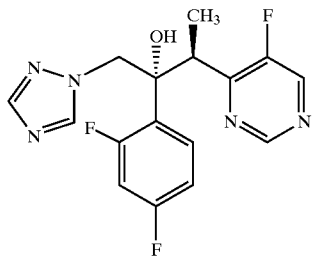

and is useful in the treatment of fungal infections. Voriconazole has a low aqueous solubility (0.2 mg/ml @ pH 3), and is not stable in water (an inactive enantiomer is formed from recombination of the retro-aldol products of hydrolysis). Thus, development of an aqueous intravenous formulation with a sufficient shelf life is difficult. These problems are magnified by the semi-polar nature of the compound (log D=1.8) which means that it is not generally solubilised by conventional means such as oils, surfactants or water miscible co-solvents.

European Patent Application 0440372 mentions that the compounds disclosed therein may be formulated with cyclodextrin: however, it is now suspected that underivatised or unmetabolised cyclodextrin has toxic effects on the body and so is unsuitable as a pharmaceutical excipient, particularly when administered parenterally.

International Patent Application WO 91/11172 discloses sulphoalkylether cyclodextrin derivatives of formula A,

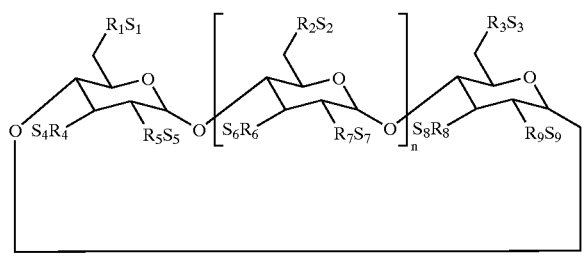

(A)

wherein n is 4, 5 or 6;

$R_{1-9}$ independently represent $O^-$ or $O-(C_{2-6}$ alkylene$)-SO^-$, provided that at least one of $R_1$ and $R_2$ is $O-(C_{2-6}$ alkylene$)-SO^-$; and $S_{1-9}$ independently represent a pharmaceutically acceptable cation (such as $H^-$ or $Na^-$).

It has now been found that the solubility of voriconazole in water can be increased by molecular encapsulation with sulphoalkylether cyclodextrin derivatives of the type disclosed in International Patent Application WO 91/11172, particularly when n is 5 (a β-cyclodextrin derivative) and the cyclodextrin ring is substituted by sulphobutyl groups.

Thus, according to the present invention, there is provided a pharmaceutical formulation comprising voriconazole, or a pharmaceutically acceptable derivative thereof and a cyclodextrin derivative of formula I,

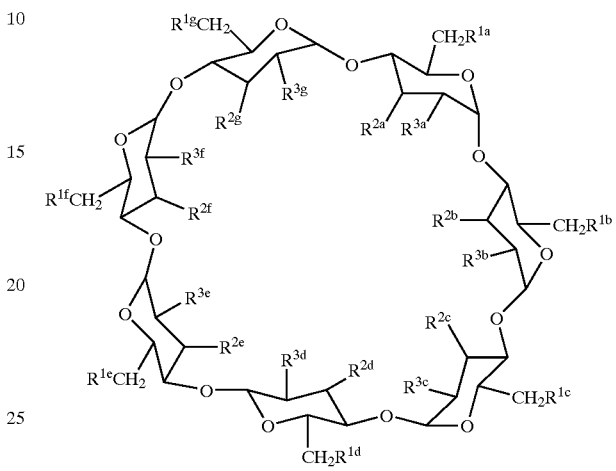

(I)

wherein $R^{1a-g}$, $R^{2a-g}$ and $R^{3a-g}$ independently represent OH or $O(CH_2)_4SO_3H$; provided that at least one of $R^{1a-g}$ represents $O(CH_2)_4SO_3H$; or a pharmaceutically acceptable salt thereof.

Pharmaceutically acceptable salts of particular interest are salts of the $O(CH_2)_4SO_3H$ groups, for example alkali metal salts, such as sodium salts.

Preferably, the average number of $O(CH_2)_4SO_3H$ groups per molecule of formula I is in the range 6.1–6.9, for example 6.5. This enhances molecular encapsulation resulting in enhanced voriconazole solubility. This effect would not be anticipated because increasing the degree of substitution increases steric hindrance around the cavity of the cyclodextrin and would be expected to reduce complexation efficiency.

It is preferred that each $O(CH_2)_4SO_3H$ present is in the form of an alkali metal salt (such as the sodium salt). This enhances the affinity of the molecule for voriconazole, which is unexpected because voriconazole is not charged.

Preferably, the formulation is for parenteral administration, for example, i.v. administration.

The aqueous stability of the voriconazole-cyclodextrin derivative complex is further enhanced by lyophilisation (freeze-drying). The cyclodextrin derivatives used in formulations according to the invention enable the finished lyophilised product to accommodate high levels of moisture (up to 3.0%) without a detrimental effect on stability. Furthermore, the use of such cyclodextrin derivatives controls and minimises the formation of the inactive enantiomer of voriconazole.

Generally, in aqueous intravenous and intramuscular formulations according to the invention, the voriconazole will be present at a concentration of from 5 mg/ml to 50 mg/ml, for example 10 mg/ml to 30 mg/ml. The cyclodextrin derivative of formula I will be present in a molar ratio of voriconazole:cyclodextrin derivative of from 1:1 to 1:10, for example 1:2 to 1:7, in particular 1:2 to 1:3. The formulations may be lyophilised (freeze dried) for storage prior to use, and made up with water when required.

In the following example, the sulphobutylether β-cyclodextrin has an average sulphobutylether substitution of 6.5 per cyclodextrin molecule, and each sulphobutylether unit is present as its sodium salt.

EXAMPLE 1 i.v. Formulation of Voriconazole

| Ingredient | Specification | mg/ml |
|---|---|---|
| Voriconazole | Pfizer | 10.000 |
| Sulphobutylether β-cyclodextrin | Pfizer | 160.000 |
| Water for injections | Ph. Eur. | to 1.000 ml |
| | Total | 1.000 ml |

Method:

1. With constant stirring, add the sulphobutylether β-cyclodextrin (SBECD) to 80% of the final volume of water for injections, and continue to stir until all the SBECD has dissolved.

2. Add the voriconazole and dissolve with stirring.

3. Make the solution up to volume with water for injections.

4. Filter the resulting solution through a sterile 0.2 mm nylon filter into a sterile container.

5. Fill 20 ml volumes into sterile freeze drying vials and stopper. Lyophilise.

What is claimed is:

1. A pharmaceutical formulation comprising voriconazole and a cyclodextrin derivative of formula I,

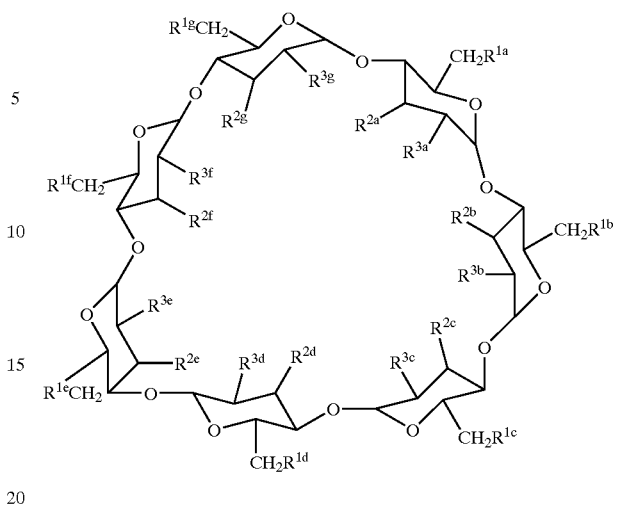

wherein
$R^{1a-g}$, $R^{2a-g}$ and $R^{3a-g}$ independently represent OH or $O(CH_2)_4SO_3H$;
provided that at least one of $R^{1a-g}$ represents $O(CH_2)_4SO_3H$;
or a pharmaceutically acceptable salt thereof;
and wherein said formulation has been lyophilized.

2. A formulation as claimed in claim 1, wherein the average number of $O(CH_2)_4SO_3H$ groups per molecule of formula I is in the range 6.1–6.9.

3. A formulation as claimed in claim 1 wherein each $O(CH_2)_4SO_3H$ present is in the form of an alkali metal salt.

4. A formulation as claimed in claim 1, which is adapted for parenteral administration.

5. A formulation as claimed in claim 1, wherein the cyclodextrin derivative of formula I is present in a molar ratio of voriconazole:cyclodextrin derivative of from 1:1 to 1:10.

6. A solution made by making up a lyophilized formulation, as claimed in claim 1, in water.

* * * * *